US009662296B2

(12) United States Patent
Roussel-Maupetit et al.

(10) Patent No.: US 9,662,296 B2
(45) Date of Patent: May 30, 2017

(54) PHARMACEUTICAL COMPOSITION COMPRISING BICARBONATE SALT, AND USE THEREOF AS A MEDICAMENT IN THE TREATMENT AND/OR PREVENTION OF URINARY LITHIASES AND RELATED DISEASES

(75) Inventors: Caroline Roussel-Maupetit, Saint-Ismier (FR); Luc-Andre Granier, Montfrin (FR); Catherine Guittet, Arles (FR)

(73) Assignee: ADVICENNE, Nimes (FR)

( * ) Notice: Subject to any disclaimer, the term of this patent is extended or adjusted under 35 U.S.C. 154(b) by 0 days.

(21) Appl. No.: 13/988,025

(22) PCT Filed: Nov. 18, 2011

(86) PCT No.: PCT/FR2011/052695
§ 371 (c)(1),
(2), (4) Date: May 17, 2013

(87) PCT Pub. No.: WO2012/066256
PCT Pub. Date: May 24, 2012

(65) Prior Publication Data
US 2013/0230590 A1    Sep. 5, 2013

(30) Foreign Application Priority Data

Nov. 18, 2010 (FR) ...................... 10 59472

(51) Int. Cl.
*A61K 9/00* (2006.01)
*A61K 9/20* (2006.01)
*A61K 9/28* (2006.01)
*A61K 31/19* (2006.01)

(52) U.S. Cl.
CPC .......... *A61K 9/0002* (2013.01); *A61K 9/2068* (2013.01); *A61K 9/2072* (2013.01); *A61K 9/2866* (2013.01); *A61K 31/19* (2013.01)

(58) Field of Classification Search
None
See application file for complete search history.

(56) References Cited

U.S. PATENT DOCUMENTS 4,451,454 A    5/1984 Wong

FOREIGN PATENT DOCUMENTS

| EP | 1 970 066 | | 9/2008 | |
|----|-----------|---|--------|---|
| EP | 1970066 | * | 9/2008 | ............ A61K 33/00 |
| EP | 1970066 A1 | | 9/2008 | |
| GB | 2 130 087 | | 5/1984 | |
| GB | 2130087 | * | 5/1984 | ............ A61K 33/10 |
| WO | 97/02017 | | 1/1997 | |
| WO | 2009/118359 | | 10/2009 | |
| WO | 2009/140341 | | 11/2009 | |

OTHER PUBLICATIONS

Breitkreutz et al. "Enteric-coated solid dosage forms containing sodium bicarbonate as drug substance:an exception from the rule?" JPP 2007, 59:59-65.*
Breitkreutz et al., "Enteric-coated solid dosage forms containing sodium bicarbonate as a drug substance: an exception from the rule?", Journal of Pharmacy and Pharmacology, 2007, vol. 59, pp. 59-65.
Information professionelle sur Nephrotrans, open drug database, ch.oddb.org.
International Search Report dated Jan. 25, 2012, corresponding to PCT/FR2011/052695.
Meka Lingam, et al.; "Preparation of a Matrix Type Multiple-Unit Gastro Retentive Floating Drug Delivery System for Captopril Based on Gas Formation Technique: In Vitro Evaluation"; vol. 9 No. 2; Jun. 1, 2008; pp. 612-619.

* cited by examiner

*Primary Examiner* — Robert A Wax
*Assistant Examiner* — Danah Al-Awadi
(74) *Attorney, Agent, or Firm* — Browdy and Neimark, PLLC

(57) ABSTRACT

A solid oral pharmaceutical composition in the form of at least one tablet, the tablet consisting of a core including at least one bicarbonate salt as active ingredient and at least one prolonged-release matrix, and of a coating including at least one coating agent, the composition allowing continuous release in vivo over a period from after a quarter of an hour and up to twelve hours after taking a single dose, for use thereof as a medicament, in particular in the treatment and/or prevention of urinary lithiasis and related diseases, occurring at a physiological pH and/or during urinary acidosis and/or during hypobicarbonataemia and/or during hypocitraturia and/or during hypercalciuria and/or during hyperoxaluria.

24 Claims, 2 Drawing Sheets

PHARMACEUTICAL COMPOSITION COMPRISING BICARBONATE SALT, AND USE THEREOF AS A MEDICAMENT IN THE TREATMENT AND/OR PREVENTION OF URINARY LITHIASES AND RELATED DISEASES

FIELD OF THE INVENTION

The present application relates to a solid pharmaceutical composition for oral use, in the form of coated, sustained-release tablets, said composition comprising at least one bicarbonate salt, used in particular for alkalization of the urine and/or treatment and/or prevention of urinary lithiases and related diseases, occurring at a physiological pH and/or during urinary acidosis and/or during hypobicarbonataemia and/or during hypocitraturia and/or during hypercalciuria and/or in hyperoxaluria.

BACKGROUND OF THE INVENTION

The urinary physiological pH is typically of the order of about 5 to 5.5.

The related diseases are generally metabolic diseases that can induce urinary lithiases as secondary symptoms. The most classical example is type 2 diabetes or fat diabetes which induces acidosis and hyperuricuria and in consequence induces urinary calculi of uric acid, which can be prevented by alkalization of the urine.

The related diseases can also be kidney diseases, as will be explained below.

Urinary lithiasis is a disease consisting of the formation of calculi in the urinary tract. A urinary calculus consists mainly of crystalline substances. Crystallization is highly dependent to saturation of the urine with crystallizable compounds such as calcium, oxalate, phosphorus, magnesium, bicarbonate, uric acid, urate, sodium or cystine. These various compounds eliminated in the urine are therefore directly involved, through their concentration and their tendency to crystallize, in the formation of calculi. However, this tendency is also influenced by various crystallization inhibiting or inducing substances. Thus, citrate and by extension the Krebs cycle precursor salts, which will increase citraturia as a secondary effect, have an inhibitory action on the formation of calculi by limiting or even preventing crystal growth, aggregation and nucleation in vitro and in vivo.

Urinary acidosis and/or hypocitraturia and/or hypercalciuria and/or hyperoxaluria are factors promoting urinary lithiasis. One treatment for certain urinary lithiases is alkalization of the urine. In fact, the solubility of certain substances, such as cystine and uric acid, is reduced in an acidic environment. Alkaline compositions comprising alkaline salts are generally indicated in the treatment of urinary acidosis. Moreover, many disorders and therapeutic situations involving the kidney or other organs can induce metabolic acidosis. For example, chronic and acute renal failure, the sequelae of renal grafts, or renal tubular acidoses, certain renal tubulopathies including cystinuria, as well as certain hereditary or non-hereditary metabolic diseases, for example hereditary distal tubular acidoses (cystinoses), diabetes and certain intoxications may be mentioned.

Alkalization should allow the urinary pH to be maintained permanently in a given range (6.5 to 7.0 in the case of oxalocalcium or uric acid crystals, 7.0 to 8.0 in the case of cystine crystals). Without treatment, the physiological pH of the urine is generally in a range from 5.0 to 5.5, or even from 5.0 to 6.0. This pH can reach a minimum value of the order of 4.4. It is all the more difficult to maintain the urinary pH at a high value when the physiological pH of the urine is low.

Among the alkaline salts used, the bicarbonate salts, and more particularly sodium bicarbonate, which is for example present in Vichy water, and potassium bicarbonate may be mentioned. Compositions comprising these salts are most often magistral preparations, with immediate effect. However, it should be emphasized that the bicarbonate salts have an unpleasant taste, making regular daily administration difficult.

A certain number of kidney diseases lead to loss of bicarbonate, such as distal tubular acidoses, kidney diseases with renal loss of bicarbonate (especially following kidney transplants or renal hypoplasia), renal failure with acidoses and Fanconi syndrome. Bicarbonate salts are commonly administered for correcting this loss of bicarbonate.

One of the advantages of the bicarbonate salts is that their absorption into the organism via the intestinal tract is independent of the pH. Another advantage of the bicarbonate salts is that they allow reinforcement of the quantity of citrate present in the urine. In fact, bicarbonate is a product of degradation of citrate in the organism. In the case of severe alkalosis (due to a high loading of bicarbonate), excretion of citrate is increased by two mechanisms: increase in endogenous synthesis of citrate and increase in secretion of citrate in the urine. Thus, bicarbonate can also be used for combating hypocitraturia.

Administration of sodium bicarbonate or potassium bicarbonate at high doses (30 to 40 grams per day) most often makes it possible to maintain urinary pH permanently above 7.6, but causes manifestations of metabolic alkalosis or digestive disorders, mainly diarrhoea.

Therefore a drawback of ingesting bicarbonate salt is its low gastric tolerance at high doses.

Administration of sodium bicarbonate or potassium bicarbonate at lower doses, from 8 to 16 grams per day in 2 to 3 liters of water well distributed over a 24-hour period, can provide alkalization of the urine. However, such a distribution over a 24-hour period requires an administration every two hours, which is very restricting for the patient. The treatment is therefore very often followed imperfectly.

Document EP 1 970 066 and especially the work by Breitkreutz et al., "*Enteric-coated solid dosage forms containing sodium bicarbonate as a drug substance: an exception from the rule?*", JPP 2007, 59: 59-65 (2007), as well as the notice given in the Compendium Suisse des Médicaments [Swiss Compendium of Medicaments], describe a medicament, Nephrotrans, in the form of soft capsules comprising sodium bicarbonate at a unit dose of 500 mg per capsule, prescribed for the treatment of metabolic hyperacidity of the blood (metabolic acidosis) and for maintenance treatment for preventing recurrence of excessive metabolic acidosis in chronic renal failure. The therapeutic use of this medicament is very different from the therapeutic use envisaged according to the present invention, namely alkalization of the urine and/or treatment and/or prevention of urinary lithiases and related diseases, occurring at a physiological pH and/or during urinary acidosis and/or during hypobicarbonataemia and/or during hypocitraturia and/or during hypercalciuria and/or during hyperoxaluria. Moreover, the medicament Nephrotrans has the particular property of being very resistant to the gastric juice. In fact, the work by Breitkreutz et al. demonstrates that, whether at pH 1 or at pH 4.5, the Nephrotrans capsule does not produce any (or hardly any) release of sodium bicarbonate for several hours. Moreover, this publication shows that Nephrotrans releases the sodium bicarbonate in 5 to 6 hours, as after 5 hours only 14-16% of the sodium bicarbonate remains in the capsule.

Moreover, the bicarbonate salt is present in a proportion (also called "loading") of about 37.5% by weight, relative to the total composition of Nephrotrans.

The bicarbonate salt according to Nephrotrans is therefore released according to the pH of the dissolution medium. In vivo, its release is therefore delayed when the product goes into the small intestine, and is limited in time. Such release certainly does not allow an alkaline urinary pH to be maintained continuously for up to 8 to 12 h.

In any case, alkalization of the urine is not optimum with the existing pharmaceutical compositions, even with proper compliance with the basic treatment. In particular, a large reduction in urinary pH is recorded during the night, the period that is most favourable to lithogenesis.

Moreover, maintaining an alkaline urinary pH over the long term presents a risk of precipitation of calcium phosphate, making the urinary calculus mixed, especially in the case of associated hypercalciuria. Finally, patients treated with Vichy water, which contains 3.5 g/L of sodium bicarbonate, can have long-term exposure to fluorosis, especially if there is renal failure.

Thus, there is still a need for a pharmaceutical composition that would advantageously permit passage of the bicarbonate salt along the whole intestinal tract in a controlled, and sustained, manner over at least about 6 to 8 hours, even more preferably over more than about 8 hours. The pharmaceutical composition according to the invention therefore generally, and particularly advantageously, permits release of the bicarbonate salt essentially over a period of about 6 to 12 h, preferably of about 8 h to 12 h.

The composition according to the invention addresses these problems, as it makes it possible to retain the advantages of the bicarbonate salts, while avoiding the drawbacks mentioned above.

SUMMARY OF THE INVENTION

The composition according to the invention is a solid pharmaceutical composition for oral use in the form of at least one tablet, said tablet being constituted by a core comprising at least one bicarbonate salt as active ingredient, preferably as the only active ingredient, and at least one sustained-release matrix, and by a coating comprising at least one coating agent, said composition permitting continuous release in vivo for a duration of after a quarter of an hour and up to twelve hours after administration of a single dose, for use as a medicament for alkalization of the urine and/or in the treatment and/or prevention of urinary lithiases and related diseases, occurring at a physiological pH and/or during urinary acidosis and/or during hypobicarbonataemia and/or during hypocitraturia and/or during hypercalciuria and/or during hyperoxaluria.

Preferably, the tablet according to the invention consists of a core and a coating.

Thus, the tablet according to the invention is coated. According to the definition of the European Pharmacopoeia (Ph. Eur.), a coated tablet is a tablet covered with one or more layers of a mixture of various substances such as natural or synthetic resins, gums, gelatin, insoluble inactive fillers, sugars, plasticizers, polyols, waxes, colourants permitted by the competent authority and, sometimes, flavourings and active substances. However, according to the invention, it is excluded that the coating comprises a bicarbonate salt.

When the coating consists of a very thin polymer film, the tablet is said to be film-coated (cf. Ph. Eur.).

Advantageously, the coating makes it possible both to mask the taste and to control the kinetics of release of the bicarbonate salt.

The European Pharmacopoeia (Ph. Eur.) defines, among tablets with modified release, sustained-release tablets, delayed-release tablets and sequential-release tablets. Modified-release tablets are tablets, coated or uncoated, that are prepared with special excipients, or by special methods, or both, with the aim of modifying the rate, the place or the moment of release of the active substance(s).

In general, sustained-release tablets are tablets permitting release of an active substance that is sustained over time and according to defined kinetics. This is preferably achieved by making a tablet core, or a plain tablet (i.e. uncoated) using a sustained-release matrix containing the active substance(s). A sustained-release matrix is generally a matrix system, most often a network polymer, whether hydrophilic or lipophilic. The diffusion of the active substance(s) within this network is generally influenced not only by the intrinsic physicochemical properties of this or these active substance(s) (such as solubility, molecular weight etc.), but also by those characterizing the matrix network (such as: hydrophilicity, degree of polymerization, gelling rate, erosion).

Advantageously, the sustained-release matrix according to the invention makes it possible to control the kinetics of release of the bicarbonate salt.

DETAILED DESCRIPTION OF THE INVENTION

The "tablet core" is, according to the invention, the whole of the tablet excluding the coating.

By "pharmaceutical composition" is meant, according to the invention, a composition the components of which are acceptable from a pharmaceutical standpoint. In particular, the composition consists of components that are suitable and acceptable for oral pharmaceutical administration.

By "component selected from the elements" is meant that the component is one of the elements or is a mixture of these elements.

The pharmaceutical composition according to the invention very advantageously permits continuous, sustained release in vivo after taking a single dose, i.e. a single administration, over a long period, generally after a quarter of an hour and up to twelve hours. Release generally begins shortly after this single administration, or most often starting from a quarter of an hour after this administration, although release can begin immediately after administration. By "continuous release" is meant, according to the invention, release that takes place constantly in vivo, from administration of the composition for a period of up to about twelve hours. The kinetics of this release is generally close to zero-order kinetics. Such a release is described as "sustained" because it reaches or exceeds a duration of one hour.

Preferably, the pharmaceutical composition according to the invention is such that it releases in vivo the majority of the bicarbonate salt (i.e. at least 50% of said salt) over a period between eight and twelve hours after a single administration of the composition.

This sustained release observed in vitro reflects controlled release in the organism, which can be verified by measuring the urinary pH of subjects treated with this composition, usually at regular intervals, for example every two hours.

Without wishing to be bound by any hypothesis, the applicant thinks that the mechanism of action is such that, when the composition is administered orally to a subject, the release of the active ingredient is controlled and sustained: the bicarbonate salt is absorbed along the whole digestive tract.

Advantageously, gastric tolerance is improved relative to the compositions known from the prior art. In fact, as release of the active ingredient generally takes place over more than eight hours, there is no intolerance to potassium or alkalosis on administration of the dose. Therefore there are no side-effects associated with metabolic alkalosis or digestive disorders, such as diarrhoea.

The composition according to the invention is particularly suitable for alkalization of the urine and/or for treatment of acidosis occurring in metabolic or renal diseases or in intoxications, and it offers more effective anti-acidosis action than the formulations of the prior art. Thus, with two administrations per day it is possible to cover the whole 24-hour period.

According to a preferred variant, the composition according to the invention is able to release (or dissolve) the bicarbonate salt in vitro in a dissolution medium of purified water at pH 7 with a dissolution apparatus of type 2, according to the European Pharmacopoeia (Ph. Eur.) 2.9.3 "*Dissolution test for solid dosage forms*", at a rate of at most 50% in 4 hours, at most 75% in 6 hours, and at most 90% in 8 hours.

Especially preferably according to the invention, independently or not of the preceding variant, the composition according to the invention is able to release (or dissolve) the bicarbonate salt in vitro in a dissolution medium of purified water at pH 7 with a dissolution apparatus of type 2, according to the European Pharmacopoeia (Ph. Eur.) 2.9.3 "*Dissolution test for solid dosage forms*", at a rate comprised within a range from 5% to 15% in one hour, at a rate comprised within a range from 35% to 55% in five hours, and at a rate comprised within a range from 70% to 90% in ten hours.

This pH of 7 is a measurement that is easy to perform in the laboratory, as it is the pH of purified water. The measurement is therefore simply carried out by dissolution in purified water.

According to a preferred variant, the composition according to the invention is able to release (or dissolve) the bicarbonate salt in vitro in a dissolution medium of solution buffered at pH 1.3 with a dissolution apparatus of type 2, according to the European Pharmacopoeia (Ph. Eur.) 2.9.3 "*Dissolution test for solid dosage forms*", at a rate of at most 50% in 4 hours, at most 75% in 6 hours, and at most 90% in 8 hours.

Especially preferably according to the invention, independently or not of the preceding variant, the composition according to the invention is able to release (or dissolve) the bicarbonate salt in vitro in a dissolution medium of solution buffered at pH 1.3 with a dissolution apparatus of type 2, according to the European Pharmacopoeia (Ph. Eur.) 2.9.3 "*Dissolution test for solid dosage forms*", at a rate comprised within a range from 5% to 15% in one hour, at a rate comprised within a range from 35% to 55% in five hours, and at a rate comprised within a range from 70% to 90% in ten hours.

In general, dissolution of the composition according to the invention in vitro in a given dissolution medium, according to the conditions described above, is independent of the pH. This means that, whatever the pH of the dissolution medium within a range between 1.3 and 7, dissolution takes place according to the same kinetics. In this case the applicant selected two different dissolution media, each characterized by its own pH, namely pH 1.3 and pH 7, for defining this profile in a characteristic manner, according to a test that is easily reproducible in vitro.

For these measurements, one gram of pharmaceutical composition, which corresponds to a unit dose, is put in a dissolution apparatus of the Pharmatest type, model PTW S3C, in which the temperature conditions are 37° C.±0.5° C., and the rotary speed is 100 rpm (revolutions per minute). The volume of the dissolution vessel is 1 L and the dissolution medium used is purified water at pH 7 or a solution buffered at pH 1.3.

The bicarbonate salt is analysed as is known to a person skilled in the art. For example, the potassium bicarbonate released is analysed by conductometry, the analytical method having been validated according to the ICH recommendations CPMP/ICH/381/95-ICH Q2 (R1).

Preferably, the salt only begins dissolving after a quarter of an hour (dissolution rate generally close to about 0%), and then the dissolution kinetics is almost of zero order.

The bicarbonate salt is preferably selected from potassium bicarbonate, sodium bicarbonate and magnesium bicarbonate, and even more preferably the bicarbonate salt is potassium bicarbonate.

The composition according to the invention most often comprises from 40% to 80%, preferably from 50 to 80%, for example from 50 to 70%, by weight bicarbonate salt based on the total weight of the composition. The bicarbonate salt is thus present at a physiologically effective dose or representing a multiple or a sub-multiple of an effective dose for a standard patient.

This represents a high level of active ingredient, by weight relative to the total weight of the composition, compared with what is known. This advantageously makes it possible to minimize the volume of the pharmaceutical composition, and therefore the volume of daily administration. As a consequence, this results in better acceptance by the patient.

This is particularly beneficial for taking the composition at high doses and/or for paediatric therapeutic treatments.

The coating agent is generally selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methyl cellulose, ethyl cellulose, xanthan gum and polyethylene oxide, waxes such as paraffin wax, beeswax or carnauba wax, ammonium methacrylate copolymers of type A and B as described in the European Pharmacopoeia, and the polyacrylates of about 30% dispersion as described in the European Pharmacopoeia. Preferably, according to the invention, the coating agent is an ethylcellulose polymer.

According to one embodiment of the invention, the coating comprises, besides a coating agent as selected from the above list, a flavouring agent and/or a colourant.

The thickness and homogeneity of the coating is one of the essential parameters of the invention, as it influences the diffusion of the bicarbonate salt through the coating and therefore the dissolution kinetics of this salt. Selection of the nature and of the amount of the coating agent used is an important parameter of the invention.

The pharmaceutical composition according to the invention generally comprises from 1% to 20%, preferably from 1.5% to 3% by weight, coating agent relative to the total weight of the composition.

The sustained-release matrix is generally a hydrophilic matrix, i.e. is formed from a material that can undergo gelling and absorb an aqueous medium, or an inert matrix, i.e. a matrix comprising excipients belonging essentially to the class of thermoplastic polymers; these polymers are generally inert with respect to biological tissues, other excipients in the formulation and the active ingredient, and they are insoluble and non-digestible in the fluids of the gastrointestinal tract. More preferably, said sustained-release matrix is selected from alginates, carboxyvinyl polymers, sodium salts of carboxymethyl cellulose, cellulose derivatives including the polymers hydroxypropyl methylcellulose, hydroxypropyl ethylcellulose, hydroxypropyl cellulose, hydroxyethyl cellulose, methyl cellulose, ethyl cellulose, and the polyacrylates with dispersion of about 30% as described in the European Pharmacopoeia, and even more preferably the sustained-release matrix is a hydroxypropyl methylcellulose.

The pharmaceutical composition according to the invention generally comprises from 10% to 30%, preferably from 15 to 25% by weight, sustained-release matrix relative to the total weight of the composition.

The pharmaceutical composition according to the invention can further comprise:

from 5% to 20%, preferably from 5% to 10% by weight, relative to the total weight of the composition, of a binder selected from microcrystalline celluloses, polyvidone, polyvinylpyrrolidone, copovidone, shellac, gelatin, polymethacrylates, synthetic resins, acrylates, maltodextrin, and starches, and preferably the binder comprises at least one microcrystalline cellulose;

from 0.01% to 5%, preferably from 0.01% to 3% by weight, relative to the total weight of the composition, of a flow agent selected from stearic acid, polyethylene glycol, magnesium stearate, calcium stearate, zinc stearate, talc, silica, hydrogenated castor oil, glyceryl behenate, and glyceryl palmitostearate, and preferably the flow agent is magnesium stearate; and/or any suitable pharmaceutical excipient, in an amount used conventionally in the field in question, for example from 0.0001% to 20% of the total weight of the composition.

The pharmaceutical excipient is generally inert, i.e. inactive and non-toxic, and acceptable from a pharmaceutical standpoint. Such an excipient is most often selected from diluents, binders, disintegrants, flow agents, lubricants, colourants permitted by the competent authority, dispersants, solubilizers, stabilizers, preservatives, plasticizers and flavouring agents. Such an excipient can also be a support, for example selected from the group comprising celluloses such as hydroxymethylcellulose, carboxymethylcellulose, cyclodextrins, polysorbate 80, mannitol, gelatin, lactose, vegetable oils, animal oils, carbonates, starches and acacia.

Preferably, all the tablets have the same composition and display a similar dissolution rate, which is the dissolution rate that can characterize the pharmaceutical composition of the invention.

According to a preferred embodiment of the invention, the pharmaceutical composition is in the form of microtablets.

The European Pharmacopoeia (Ph. Eur.) defines a tablet as a solid preparation containing a unit dose of one or more active substances. Tablets are obtained by agglomerating a constant volume of particles by compression, or by some other suitable method of manufacture such as extrusion, moulding or freeze-drying (lyophilization). Tablets are intended for the oral route. Tablets are generally in the form of a right cylinder, the lower and upper faces of which can be flat or convex and the edges bevelled. The size of a tablet, or average dimension, is therefore generally the diameter of this cylinder, or an equivalent. However, if the height of the cylinder is significant, and greater than the diameter of the cylinder, the size of the tablet is the height of this cylinder.

By "microtablet" is meant, according to the invention, a tablet with a size comprised within a range from 2 to 4 mm (generally with the size accurate to ±10%). Preferably, all the microtablets have the same composition and they have a similar dissolution rate, which is the dissolution rate that can characterize the pharmaceutical composition of the invention. This dissolution rate is commonly established on the basis of one unit of the preparation or, in the context of the invention, one gram of microtablets.

Owing to the small size of the microtablet, a single microtablet will not be sufficient for one administration, and several microtablets will be administered for each dose.

An advantage of the microtablet form is that patients find them easier to take, compared with taking a single tablet of larger volume. This is particularly advantageous when the patient is a child.

It is understood that, according to the invention, the patient will be able to ingest several microtablets at each administration, depending on the therapeutic dose that is suitable for him (the daily dose divided by the number of administrations per day). Thus, one administration of the medicament corresponds to several microtablets, i.e. a set of microtablets. The invention therefore also aims to cover a set of microtablets, corresponding to a therapeutic administration. A person skilled in the art is able to evaluate the number of microtablets corresponding to a therapeutic dose, as a function of the needs of the person, their age, their weight, as a function of the amount of bicarbonate salt per microtablet, as well as the number of doses per day.

The composition according to the invention is not limited to a presentation in the form of microtablets. The composition according to the invention is more generally, in the context of the invention, in the form of tablets. The size of said tablets is generally at least 2 mm, for example comprised within a range from 2 to 25 mm. A person skilled in the art is able to select the size of tablet. These tablets can be microtablets, or tablets of larger size, for example comprised within a range from 4 to 25 mm.

The tablets according to the invention are coated, which permits masking of the taste.

The tablets according to the invention are particularly suitable for alkalization of the urine, for treatment of urinary lithiases and related diseases, occurring at a physiological pH and/or during urinary acidosis and/or during hypobicarbonataemia and/or during hypocitraturia and/or during hypercalciuria and/or during hyperoxaluria, owing to their optimum release profile.

The composition according to the present invention can be used in mammals, more precisely in humans, and quite particularly in children.

The method of manufacture of the pharmaceutical composition according to the invention generally comprises the three successive steps described below:

The first step is a step of mixing the active ingredient, preferably the single active ingredient, with the other ingredients constituting the core of the pharmaceutical composition according to the invention. Mixing is carried out for example in a gravity-fed mixer of the Stuart STR4 type, but can be carried out in any other type of industrial mixer.

The second step is a step of tablet manufacture, from the mixture originating from the first step, generally carried out by a first operation of direct compression in a rotary press, for example for manufacturing microtablets of size 2 mm (of the PR12 type) using six supports each having a head with six 2-mm punches. This second step then comprises a second operation of dedusting of the tablets produced during the first operation.

The third step is a step of coating, with the coating agent, of the tablets originating from the second step. The coating agent is generally applied in the form of solution or suspension under conditions that promote evaporation of the solvent.

According to one embodiment of the invention, the composition comprises from 60% to 70% potassium bicarbonate, from 15 to 25% hypromellose, from 7 to 17% microcrystalline cellulose, from 1 to 3% glyceryl behenate, from 0.01% to 1% magnesium stearate, and from 1.5 to 3% ethyl cellulose, relative to the total weight of the composition.

BRIEF DESCRIPTION OF THE DRAWINGS

The invention is illustrated in the attached FIGS. 1 and 2.

FIG. 1 is referred to in Example 1 below.

FIG. 2 is referred to in Example 2 below.

The following examples illustrate the invention without however limiting it.

Example 1

Batch I: Curve I

A batch I of microtablets of 2 mm size (average diameter) was produced according to the method described above, namely a step of mixing the powders, followed by a compression step, then a coating step, at a rate of 2000 g of microtablets per batch. These tablets have the following composition:

Potassium bicarbonate (active ingredient, source Dr Paul Lohmann): 66.4%

Hypromellose (matrix, HPMC 100 000 90SH0): 19.5%

Hypromellose is a hydroxypropyl methylcellulose.

Microcrystalline cellulose (binder, commercial reference Ceolus® UF-711 from the company Asahi-Kasei): 9.8%

Magnesium stearate (flow agent): 0.01%

Glyceryl behenate (lubricant, commercial reference Compritol® ATO 888 from the company GATTEFOSSE): 2%

Ethyl cellulose (polymer) (coating material, commercial reference Ethocel® 20 standard premium from the company Dow Chemical): 2.3%.

Figure 1:
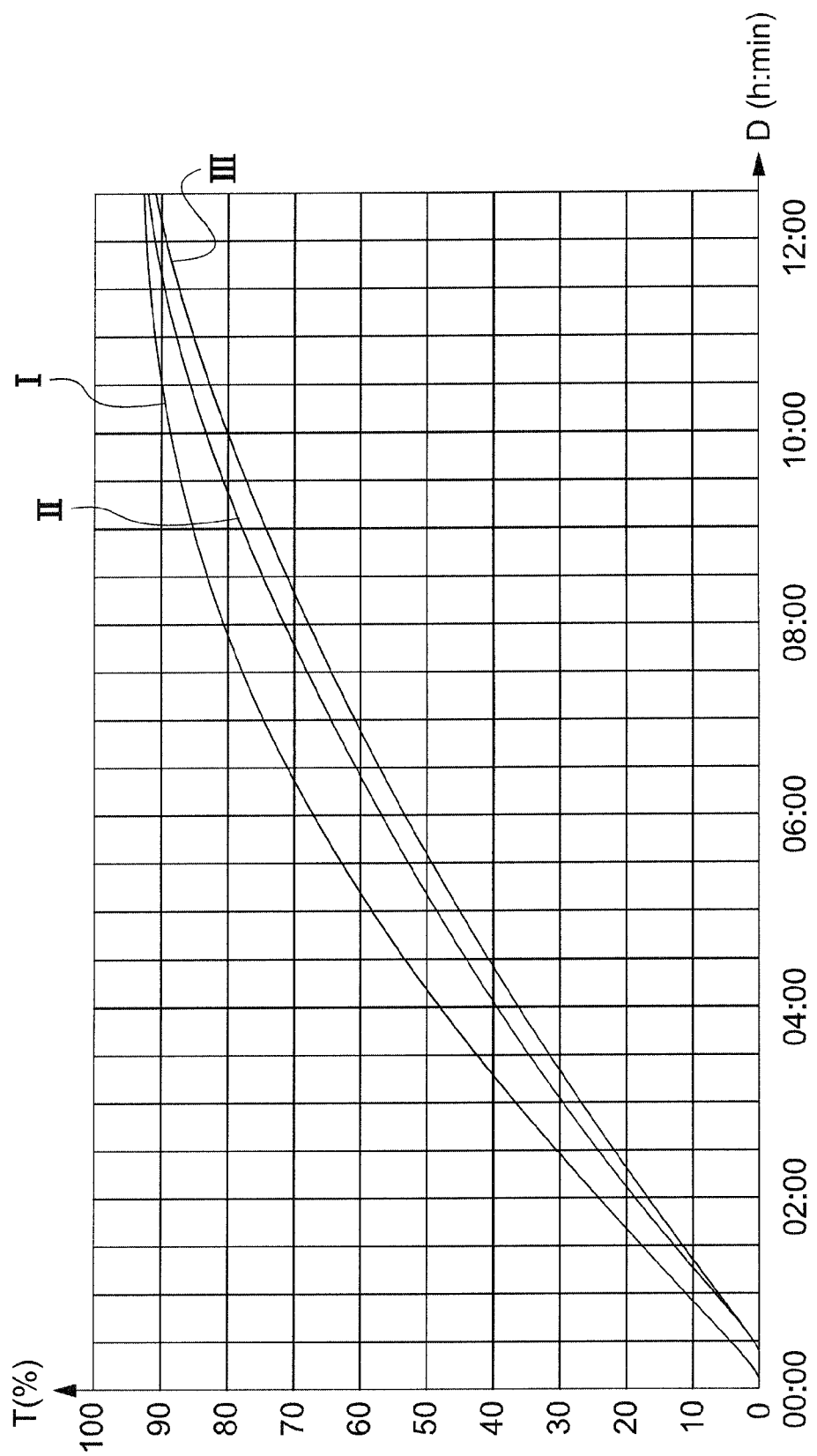
FIG. 1 shows the dissolution profile as the dissolution rate T (percentage of active ingredient: potassium bicarbonate) as a function of time D (h:min) for three different compositions identified by I, II and III.

Curve I in FIG. 1 shows the in vitro dissolution profile of these microtablets in purified water at pH 7.

Such a profile was obtained by placing the mini-tablets in a Pharmatest dissolution apparatus, model PTW S3C, at a temperature of 37° C.±0.5°, with a volume of the dissolution vessel of 1 L and at a rotary speed of 100 rpm.

The potassium bicarbonate is analysed by conductometry according to an analytical method validated according to the ICH recommendations CPMP/ICH/381/95-ICH Q2 (R1).

Batch II: Curve II

A batch II of microtablets of 2 mm size (average diameter) was produced according to the method described above, namely a step of mixing the powders, followed by a compression step, then a coating step, at a rate of 1000 g of microtablets per batch. These tablets have the following composition:

Potassium bicarbonate (active ingredient, source Dr Paul Lohmann): 68.4%

Hypromellose (matrix, HPMC 100 000 90SH): 19.6%

Microcrystalline cellulose (binder, commercial reference Ceolus® UF-711 from the company Asahi-Kasei): 9.8%

Magnesium stearate (flow agent): 0.06%

Ethyl cellulose (polymer) (coating material, commercial reference Ethocel® 20 standard premium from the company Dow Chemical): 2.3%.

Curve II in FIG. 1 shows the in vitro dissolution profile of these microtablets in purified water at pH 7. This profile and analysis of potassium bicarbonate were performed as for batch I.

Batch III: Curve III

A batch III of microtablets of 2 mm size (average diameter) was produced according to the method described above, namely a step of mixing the powders, followed by a compression step, then a coating step, at a rate of 2000 g of microtablets per batch. These tablets have the following composition:

Potassium bicarbonate (active ingredient, source Dr Paul Lohmann): 66.4%

Hypromellose (matrix, HPMC 100 000 90SH): 19.5%

Microcrystalline cellulose (binder, commercial reference Ceolus® UF-711 from the company Asahi-Kasei): 9.8%

Magnesium stearate (flow agent): 0.01%

Glyceryl behenate (lubricant, commercial reference Compritol® ATO 888 from the company GATTEFOSSE): 2%

Ethyl cellulose (polymer) (coating material, commercial reference Ethocel® 20 standard premium from the company Dow Chemical): 2.3%.

Curve III in FIG. 1 shows the in vitro dissolution profile of these microtablets in purified water at pH 7.

Such a profile and analysis of potassium bicarbonate were achieved as for batch I.

The microtablets I, II and III are very well accepted and tolerated by the subjects. Moreover, they have no taste and are easy to swallow.

Curves I, II and III have substantially similar shapes, and each of the dissolution profiles corresponding to these curves I, II and III comply with the preferred conditions claimed for the composition of the present invention.

Thus, each of the three curves I, II and III illustrates release of potassium bicarbonate that is gradual and even, meeting the criteria of a rate of at most 50% in 4 hours, at most 75% in 6 hours, and at most 90% in 8 hours.

Moreover, each of the three curves I, II and III illustrates release of potassium bicarbonate that leads to almost complete dissolution after 12 to 15 hours.

Example 2

Two batches A and D of tablets of 12 mm size (average diameter) were produced according to the method described above, namely a step of mixing the powders, followed by a compression step, then a coating step, at a rate of 200 g of tablets per batch. These tablets have the following composition:

Curve A: Batch A

Potassium bicarbonate (active ingredient, source Dr Paul Lohmann): 56%

Hypromellose (sustained-release matrix, HPMC 100 000 90SH, source SEPPIC): 25%

Carnauba wax (coating material): 19%

Curve D: Batch D

Potassium bicarbonate (active ingredient, source Dr Paul Lohmann): 71%

Hypromellose (sustained-release matrix, HPMC 100 000 90SH, source SEPPIC): 10%

Carnauba wax (coating material): 19%

Figure 2:
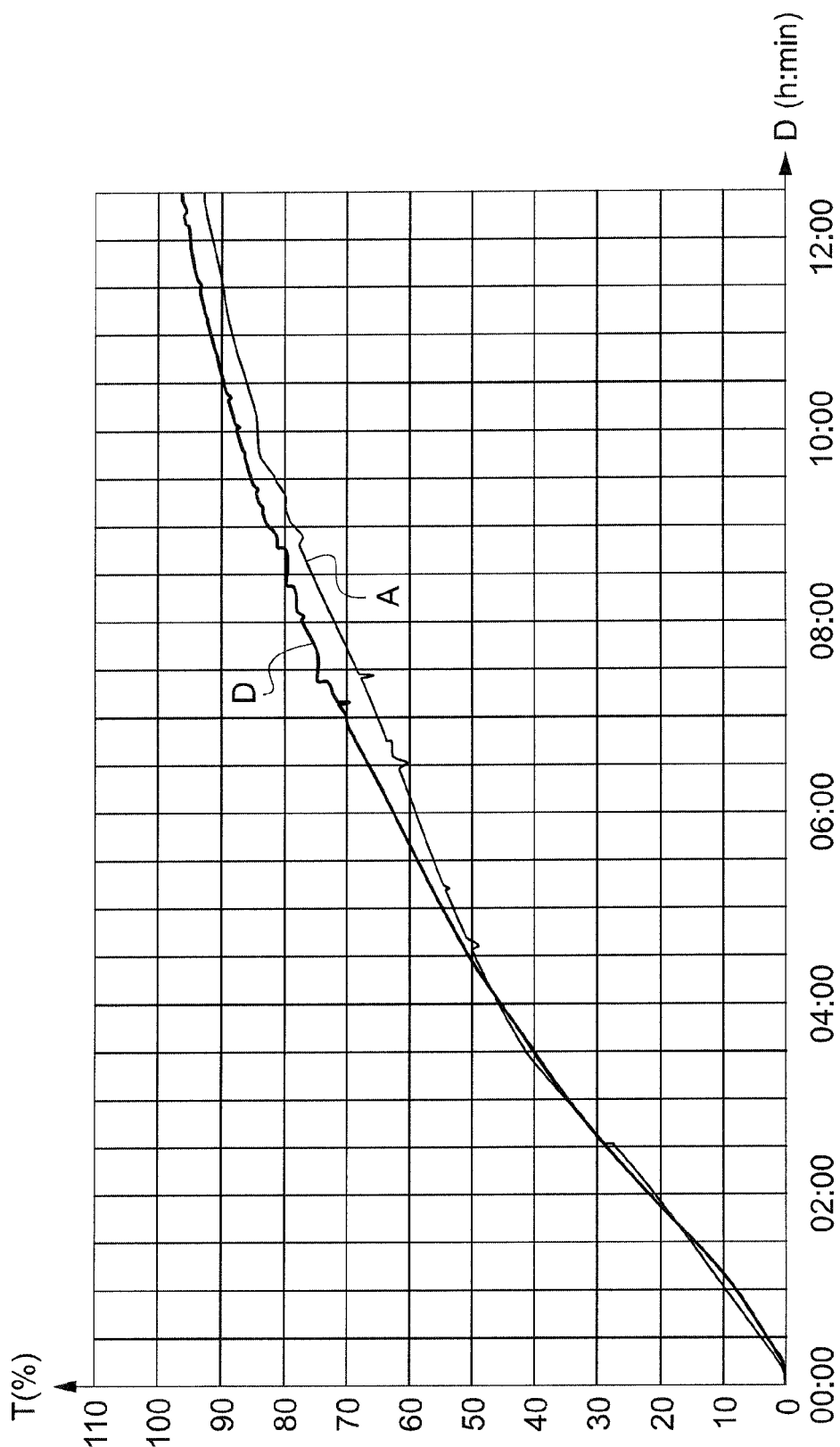
FIG. 2 shows the dissolution profile as dissolution rate T (percentage of active ingredient: potassium bicarbonate) as a function of time D (h:min) for two different compositions identified by A and D.

Curves A and D in FIG. 2 show the in vitro dissolution profiles of such 12-mm tablets in purified water at pH 7. The tablets are put in a Pharmatest dissolution apparatus, model PTW S3C, in which the temperature conditions are 37° C.±0.5°, the volume of the dissolution vessel is 1 L and the rotary speed is 100 rpm.

The potassium bicarbonate is analysed by conductometry according to an analytical method validated according to the ICH recommendations CPMP/ICH/381/95-ICH Q2 (R1).

Tablets A and D are very well accepted and tolerated by the subjects. Moreover, they have no taste and are easy to swallow.

Curves A and D have substantially similar shapes, and each of these dissolution profiles A and D complies with the preferred conditions claimed for the composition of the present invention.

Thus, each of the two curves A and D illustrates release of potassium bicarbonate that takes place gradually and evenly, meeting the criteria of a rate of at most 50% in 4 hours, at most 75% in 6 hours, and at most 90% in 8 hours.

Moreover, each of the two curves D and A illustrates release of potassium bicarbonate that leads to almost complete dissolution after 12 to 15 hours.

The invention claimed is:

1. Solid pharmaceutical composition for oral administration in the form of a tablet, said tablet consisting of:
   (i) a core comprising from 40% to 80% by weight of at least one bicarbonate salt as the sole active ingredient, the salt being selected from the group consisting of potassium bicarbonate, sodium bicarbonate and magnesium bicarbonate,
   and a sustained-release matrix comprising from 10% to 30% by weight of at least one selected from the group consisting of sodium salts of carboxymethyl cellulose, hydroxypropyl methylcellulose, hydroxypropyl cellulose, hydroxyethyl cellulose, methyl cellulose, and combinations thereof; and
   (ii) a coating comprising from 1% to 20% by weight of at least one pH independent coating agent selected from the group consisting of ethyl cellulose, waxes, ammonium methacrylate copolymers of type A and type B, polyacrylates of about 30% dispersion, and combinations thereof,
   each of said percentages by weight being relative to the total weight of the composition,
   said composition providing continuous release in vivo of said bicarbonate salt over a period of 15 minutes to twelve hours after the oral administration of a single dose of said composition to a subject,
   wherein the composition has a dissolution profile that has pH-independent kinetics, and
   wherein the composition is able to release the bicarbonate salt in vitro in a dissolution medium of purified water at pH 7 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours, and
   the composition is able to release the bicarbonate salt in vitro in a dissolution medium of solution buffered at pH 1.3 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours.

2. The composition according to claim 1, wherein the composition further comprises from 5% to 20% by weight, relative to the total weight of the composition, of a binder selected from the group consisting of microcrystalline celluloses, polyvidone, polyvinylpyrrolidone, copovidone, shellac, gelatin, polymethacrylates, synthetic resins, acrylates, maltodextrin, and starches.

3. The composition according to claim 1, wherein the composition further comprises from 0.01% to 5% by weight, relative to the total weight of the composition, of a flow agent selected from the group consisting of stearic acid, polyethylene glycol, magnesium stearate, calcium stearate, zinc stearate, talc, silica, hydrogenated castor oil, glyceryl behenate, and glyceryl palmitostearate.

4. The composition according to claim 1, wherein said tablet has a size within a range of 2 pm to 25 mm.

5. The composition according to claim 1, wherein the composition comprises from 60% to 70% potassium bicarbonate, from 15% to 25% hydroxypropyl methylcellulose, from 7% to 17% microcrystalline cellulose, from 1% to 3% glyceryl behenate, from 0.01% to 1% magnesium stearate, and from 1.5% to 3% ethyl cellulose, relative to the total weight of the composition.

6. The composition according to claim 1, wherein the at least one bicarbonate salt is potassium bicarbonate.

7. The composition according to claim 1, wherein the composition comprises from 50% to 80% by weight bicarbonate salt based on the total weight of the composition.

8. The composition according to claim 1, wherein the composition comprises from 15% to 25% by weight of the sustained-release matrix relative to the total weight of the composition.

9. The composition according to claim 2, wherein the composition further comprises from 5% to 10% by weight, relative to the total weight of the composition, of microcrystalline cellulose.

10. The composition according to claim 1, wherein the composition further comprises from 0.01% to 3% by weight, relative to the total weight of the composition, of magnesium stearate.

11. A solid pharmaceutical composition for oral administration in the form of a tablet, the tablet comprising:
   a core comprising from 50% to 80% by weight of at least one bicarbonate salt selected from the group consisting of potassium bicarbonate, sodium bicarbonate and magnesium bicarbonate, and a sustained-release matrix comprising from 15% to 25% by weight of hydroxypropyl methylcellulose; and
   a coating comprising from 1.5% to 3% by weight of ethyl cellulose,
   each of said percentages by weight being relative to the total weight of the composition
   said composition providing continuous release in vivo of said bicarbonate salt over a period of 15 minutes to twelve hours after the oral administration of a single dose of said composition to a subject,
   wherein the composition has a dissolution profile that has pH-independent kinetics, and
   wherein the composition is able to release the bicarbonate salt n vitro in a dissolution medium of purified water at pH 7 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours, and the composition is able to release the bicarbonate salt in vitro in a dissolution medium of solution buffered at pH 1.3 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours.

12. The composition according to claim 11, wherein the core comprises 60% to 70% by weight of potassium bicarbonate.

13. The composition according to claim 12, wherein the composition further comprises from 5% to 10% by weight of microcrystalline cellulose, and from 0.01% to 3% by weight of magnesium stearate, each of said percentages by weight being relative to the total weight of the composition.

14. A solid pharmaceutical composition for oral administration in the form of a tablet, the tablet comprising:
    a core comprising from 50% to 80% by weight of at least one bicarbonate salt as the sole active ingredient and which is selected from the group consisting of potassium bicarbonate, sodium bicarbonate and magnesium bicarbonate, and a sustained-release matrix comprising from 10% to 30% by weight of hydroxypropyl methylcellulose; and
    a coating comprising from 1 to 20% by weight of wax, each of said percentages by weight being relative to the total weight of the composition
    said composition providing continuous release in vivo of said bicarbonate salt over a period of 15 minutes to twelve hours after the oral administration of a single dose of said composition to a subject,
    wherein the composition has a dissolution profile that has pH-independent kinetics, and
    wherein the composition is able to release the bicarbonate salt in vitro in a dissolution medium of purified water at pH 7 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours, and
    the composition is able to release the bicarbonate salt in vitro in a dissolution medium of solution buffered at pH 1.3 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours.

15. The composition according to claim 14, wherein the bicarbonate salt is potassium bicarbonate.

16. The composition according to claim 14, wherein the coating comprises about 19% by weight of carnauba wax.

17. A method of treating alkalization of the urine and/or treating or reducing the incidence of urinary lithiasis and related diseases in a subject, comprising administering to a subject in need thereof an effective amount of the pharmaceutical composition of claim 1.

18. Solid pharmaceutical composition for oral administration in the form of a tablet, said tablet consisting of:
    a core comprising from 40% to 80% by weight of at least one bicarbonate salt as an active ingredient, the salt being selected from the group consisting of potassium bicarbonate, sodium bicarbonate and magnesium bicarbonate;
    a sustained-release matrix comprising from 10% to 30% by weight of hydroxypropyl methylcellulose polymer; and
    a coating comprising from 1.5% to 3% by weight of ethyl cellulose polymer,
    each of said percentages by weight being relative to the total weight of the composition,
    said composition providing continuous release in vivo of said bicarbonate salt over a period of 15 minutes to twelve hours after the oral administration of a single dose of said composition to a subject,
    wherein the composition has a dissolution profile that has pH-independent kinetics, and
    wherein the composition is able to release the bicarbonate salt in vitro in a dissolution medium of purified water at pH 7 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours, and
    the composition is able to release the bicarbonate salt in vitro in a dissolution medium of solution buffered at pH 1.3 with a dissolution apparatus of type 2, according to the European Pharmacopoeia 2.9.3 "Dissolution test for solid dosage forms", at a rate within a range of 5% to 15% in one hour, at a rate within a range of 35% to 55% in five hours, and at a rate within a range of 70% to 90% in ten hours.

19. The composition according to claim 18, said tablet consisting of:
    a core comprising from 60% to 70% by weight of potassium bicarbonate;
    a sustained-release matrix comprising from 15% to 25% by weight of hydroxypropyl methylcellulose; and
    a coating comprising from 1.5% to 3% by weight of ethyl cellulose;
    the composition further comprising:
    a binder comprising from 7% to 17% microcrystalline cellulose; and
    a flow agent comprising from 1% to 3% glyceryl behenate and from 0.01% to 1% magnesium stearate,
    each of said percentages by weight being relative to the total weight of the composition.

20. The composition according to claim 14, wherein the coating comprises from 1 to 20% by weight of carnauba wax.

21. The solid pharmaceutical composition of claim 11, wherein said at least one bicarbonate salt is the sole active ingredient.

22. The solid pharmaceutical composition of claim 18, wherein said at least one bicarbonate salt is the sole active ingredient.

23. The solid pharmaceutical composition of claim 1, wherein said wax is paraffin wax.

24. The solid pharmaceutical composition of claim 1, wherein said wax is carnauba wax.

* * * * *